United States Patent
Sharma et al.

(10) Patent No.: US 9,968,537 B2
(45) Date of Patent: May 15, 2018

(54) ANTI-DANDRUFF COMPOSITIONS AND HAIR CARE FORMULATIONS CONTAINING ZINC PYRITHIONE AND QUATERNARY AMMONIUM SALT

(71) Applicant: JUBILANT LIFE SCIENCES LIMITED, Noida, Uttar Pradesh (IN)

(72) Inventors: Vineet Sharma, Uttar Pradesh (IN); Ashutosh Agarwal, Uttar Pradesh (IN)

(*) Notice: Subject to any disclaimer, the term of this patent is extended or adjusted under 35 U.S.C. 154(b) by 0 days. days.

(21) Appl. No.: 14/916,267

(22) PCT Filed: Sep. 2, 2014

(86) PCT No.: PCT/IN2014/000570
§ 371 (c)(1),
(2) Date: Mar. 3, 2016

(87) PCT Pub. No.: WO2015/033351
PCT Pub. Date: Mar. 12, 2015

(65) Prior Publication Data
US 2016/0220468 A1 Aug. 4, 2016
US 2016/0374914 A2 Dec. 29, 2016

(30) Foreign Application Priority Data

Sep. 6, 2013 (IN) .......................... 2640/DEL/2013

(51) Int. Cl.
| | |
|---|---|
| A61K 8/58 | (2006.01) |
| A01N 33/08 | (2006.01) |
| A01N 33/12 | (2006.01) |
| A01N 43/40 | (2006.01) |
| A01N 59/16 | (2006.01) |
| A61K 8/41 | (2006.01) |
| A61Q 5/00 | (2006.01) |
| A61K 8/34 | (2006.01) |
| A61K 8/49 | (2006.01) |

(52) U.S. Cl.
CPC .............. *A61K 8/58* (2013.01); *A01N 33/08* (2013.01); *A01N 33/12* (2013.01); *A01N 43/40* (2013.01); *A01N 59/16* (2013.01); *A61K 8/345* (2013.01); *A61K 8/41* (2013.01); *A61K 8/416* (2013.01); *A61K 8/4926* (2013.01); *A61K 8/4933* (2013.01); *A61Q 5/006* (2013.01); *A61K 2800/262* (2013.01); *A61K 2800/524* (2013.01); *A61K 2800/591* (2013.01)

(58) Field of Classification Search
CPC .......................... A61K 2800/58; A61K 31/555
See application file for complete search history.

(56) References Cited

U.S. PATENT DOCUMENTS

| | | | |
|---|---|---|---|
| 3,489,686 A | 1/1970 | Parran, Jr. | |
| 3,580,853 A | 5/1971 | Parran, Jr. | |
| 3,636,213 A | 1/1972 | Gerstein et al. | |
| 3,761,417 A | 9/1973 | Parran, Jr. | |
| 3,785,985 A | 1/1974 | Grand | |
| 3,940,482 A | 2/1976 | Grand | |
| 4,396,766 A * | 8/1983 | Farmer, Jr. ........... | C07D 213/89 546/290 |
| 4,557,928 A | 12/1985 | Glover | |
| 4,835,129 A * | 5/1989 | Travers .................... | B01J 29/90 502/37 |
| 4,835,149 A | 5/1989 | Burke et al. | |
| 6,908,912 B2 | 6/2005 | Rioux et al. | |
| 8,206,694 B2 | 6/2012 | Chang et al. | |
| 8,506,942 B2 | 8/2013 | Burry et al. | |
| 2002/0168327 A1* | 11/2002 | Bailey .................... | A61K 8/365 424/70.1 |
| 2003/0228272 A1 | 12/2003 | Amjad et al. | |
| 2004/0058855 A1 | 3/2004 | Schwartz et al. | |
| 2005/0158263 A1 | 7/2005 | Rioux et al. | |
| 2006/0182696 A1 | 8/2006 | Patil et al. | |
| 2006/0241190 A1 | 10/2006 | Munisekhar | |
| 2007/0020221 A1 | 1/2007 | Bissett | |
| 2008/0057015 A1 | 3/2008 | Oblong et al. | |
| 2011/0287074 A1 | 11/2011 | Jin et al. | |
| 2011/0318434 A1 | 12/2011 | Guthery | |
| 2012/0012172 A1 | 1/2012 | Schmidt et al. | |
| 2012/0064136 A1 | 3/2012 | Baker, Jr. et al. | |
| 2012/0100092 A1 | 4/2012 | Murray et al. | |

FOREIGN PATENT DOCUMENTS

| | | |
|---|---|---|
| EP | 0034385 A2 | 8/1981 |
| EP | 0941061 A1 | 9/1999 |
| WO | 97/03637 A1 | 2/1997 |
| WO | 98/23258 A1 | 6/1998 |
| WO | 01/95717 A2 | 12/2001 |
| WO | 2013/072163 A2 | 5/2013 |

\* cited by examiner

*Primary Examiner* — San Ming R Hui

(57) ABSTRACT

The present invention discloses a stable biocidal composition with enhanced antifungal activity at low concentration of active (s) and a process for preparing the same. The composition comprises: zinc pyrithione, C8-C18 quaternary ammonium salt (preferably cetylpyridinium chloride), water miscible glycol/polyol/glycol ether/lactam, organic amine and/or alkanol amine. The composition can be formulated into: hair care formulations, antidandruff hair care formulations, water based paints, coatings, adhesives, hard surface cleaners, fabric care compositions, wood products, plastic products and medical products. The biocidal compositions and the resulting formulations are transparent or opaque and are stable at varying pH and humidity conditions.

21 Claims, No Drawings

ANTI-DANDRUFF COMPOSITIONS AND HAIR CARE FORMULATIONS CONTAINING ZINC PYRITHIONE AND QUATERNARY AMMONIUM SALT

CROSS REFERENCE TO RELATED APPLICATIONS

This application is a National Stage of International Application No. PCT/IN2014/000570, filed on Sep. 2, 2014, which claims priority to Indian patent application no. 2640/DEL/2013, filed on Sep. 6, 2013, the disclosures of which are incorporated by reference in their entirety.

FIELD OF INVENTION

The present invention relates to a stable, transparent or opaque biocidal compositions comprising zinc pyrithione alone or in combination with a $C_8$-$C_{18}$ quaternary ammonium salt, preferably cetylpyridinium chloride. The compositions possess higher bio-availability and enhanced antifungal activity and are capable for being formulated into various personal care and industrial formulations.

BACKGROUND OF THE INVENTION

Zinc pyrithione (ZPTO), also known as zinc pyridine-2-thiol-N-oxide or bis-[1-hydroxy-2(H) pyridinethionato]-zinc is a broad spectrum antimicrobial agent and has been used as fungicide and bactericide in various personal care and pharmaceutical products, particularly in anti-dandruff shampoos. ZPTO is also used as a biologically active agent for cutting oils and coolant systems, as an agent for protecting cellulosic fibres from loss of tensile strength due to action of fungi and as a preservative for water based paints, coatings, adhesives, wet-state preservatives, hard surface cleaners, fabric care compositions, wood products, plastic products, medical products, fibres or any other application where microorganism growth must be stopped or slowed.

The antifungal and antimicrobial activity of ZPTO depends on the bio-availability of ZPTO molecule on scalp. Because of poor solubility in water (6-12 ppm), the concentration of ZPTO molecules in aqueous media and thereafter on hair and scalp also remains low, leading to poor bio-availability. Also, when used in personal care formulations, it produces white suspension that precipitate in the packaging bottle. Therefore, to overcome these disadvantages of low water solubility, precipitations and poor bio-availability, ZPTO is generally used in excess (1-2% w/w) but higher concentration of ZPTO lacks ready consumer acceptability due to harshness.

There had been many approaches to increase the solubilisation and antimicrobial efficacy of zinc pyrithione.

U.S. Pat. No. 3,636,213 discloses solubilisation of heavy metal pyrithione salts in common organic solvents and/or water by combination with primary alkyl and aryl monoamines or, polyalkyleneimines, preferably dodecyl amine and diglycol amine for use in hair dressings. The compositions have pH's from about 8.5-9.0.

U.S. Pat. No. 3,785,985 and U.S. Pat. No. 3,940,482 describe the solubilization of heavy metal pyrithione salts in water and detergent containing compositions with aliphatic polyamine. However, ZPTO solubilized in alcohol/water system using polyethylenimine has pH of about 9.0 or above and reducing pH less than 8.0 leads to precipitation of ZPTO in the system.

U.S. Pat. No. 4,835,149 discloses the use of alkanol and/or alkyl amines in the solublizing a metal pyrithione salt in the preparation of a shampoo effective for the treatment of seborrhea and dandruff. The amines include ethanolamine, diethanolamine, monoisopropylamine and others together with a cosmetically effective amount of an aminopolycarboxylic acid to regulate the pH of the system between 6.5-7.5.

U.S. Pat. No. 6,908,912 discloses a stable, soluble, antimicrobial composition where insoluble metal salts of pyrithione in combination with a zinc source (zinc salts, -oxides, -hydroxides, -borates, -sulfates, -chlorides etc.) were solubilised in an organic amine (1,2-alkanolamines and 1,3-alkanolamines) alone or in combination with a second organic amine (monomeric and polymeric forms of 1,2-alkyldiamines and 1,3-alkyldiamines). These compositions deliver higher concentration of pyrithione and zinc ions to an application (in-can preservatives and metalworking fluids) and thus provide enhanced biocidal efficacy against microorganisms and bio-films.

It is known that below pH 4.5 zinc complex dissociates into free pyrithione and above pH 9.5, zinc complex hydrolyzes to yield ionized pyrithione and zincate species. Both free and ionized pyrithione are biologically active but being much more water soluble than the zinc complex they are most susceptible to degradation from exposure to light or oxygen. In the patent applications cited above, where different types of amines have been used to solubilize ZPTO, either require pH adjustment, pre-formulation of the actives or give precipitate on pH adjustment. Also these prior arts do not disclose any improved or enhanced antifungal or antimicrobial activity particularly the anti-dandruff efficacy for the resulting solubilized ZPTO as compared to ZPTO suspensions. Further, it is extremely difficult to simultaneously attain superior hair sensory attributes along with higher anti-dandruff efficacy from ZPTO containing compositions (US 2006/0182696).

WO 20010095717 discloses that cationic polymers can increase the efficacy of zinc pyrithione in an anti-dandruff shampoos by enhancing the deposition and retention of the water insoluble ZPTO particles on scalp. Similarly polyethylenimine or the reaction product of polyethylenimine and ethylene oxide or propylene oxide (U.S. Pat. No. 3,489,686); water-soluble cationic nitrogen-containing polymers or nitrogen-substituted cellulose ether derivatives (U.S. Pat. No. 3,580,853) and piperidinum chloride (U.S. Pat. No. 3,761,417) have also been disclosed to increase the efficacy of ZPTO. However, the effect on adsorption of a metal pyrithione salt such as zinc pyrithione was not found sufficient for required or enhanced anti-dandruff efficacy.

U.S. Pat. No. 4,557,928 describes the use of acrylamide copolymer quaternium 41 and Methocel to create more efficacious zinc pyrithione anti-dandruff shampoo but these shampoos were found unstable over a long period of time.

Cationic surfactants such as amino or quaternary ammonium hydrophilic moieties has been used as cationic surfactant or emulsifying agent in hair conditioners, shampoos, anti-static formulations, fabric softeners and other cosmetics and toiletries preparations (EP 0034385, EP 0941061, US 2008/0057015, U.S. Pat. No. 8,506,942, US 2012/0064136, U.S. Pat. No. 8,206,694 and US 2012/0100092). Some of them like cetyl pyridinium chloride, is also commonly used as antiseptic and/or antimicrobial component at low concentrations (0.025-0.1%) in many OTC health care products (creams, dentifrices, deodorizing and antiperspirant preparations mouth washes, toothpastes, lozenges, throat sprays, cough syrups, nasal sprays and pre-moistened wipes) deodorant.

US 2007/0020221 describes the use of cetylpyridinium chloride (CPC) as a skin lightening or pigmentation reducing cosmetic agent in cosmetic compositions to regulate the condition of mammalian keratinous tissue particularly for preventing, retarding, and/or treating uneven skin tone.

US 2006/0241190 describes the specific utility of cetylpyridinium chloride in cosmetic compositions as a keratolytic active with SLES for the treatment of psoriasis, eczema and like skin disorders.

As antimicrobial active in shampoos and/or hair care products, US 2011/0287074 describes the use of CPC as secondary antimicrobial agent in the form of a microemulsion. US 2012/012172 provides an antimicrobial composition with a synergistic effect of laurylamine oxide and CPC. This composition which has strong antimicrobial efficacy can be incorporated into shampoos for the treatment of fungal and/or bacterial infection on skin or mucosal surfaces.

Although the prior art describes that cationic polymers can enhance the deposition of ZPTO on scalp, it is extremely difficult to formulate their stable composition as they show problems in formulation compatibility particularly with ZPTO, resulting in loss of transparency, drop in viscosity and instability over a long period of time.

Thus, there is a need to develop antimicrobial stock compositions and/or personal care formulations with ZPTO in such a manner that ZPTO remains solubilised, maintains transparency above 90%, remains stable in wide pH range and storage conditions, aesthetically more desirable and simultaneously imparts high anti-dandruff efficacy at low concentration of active(s).

SUMMARY OF THE INVENTION

The present invention is directed to transparent or opaque biocidal compositions and their formulations, said composition comprising zinc pyrithione either alone or in combination with a $C_8$-$C_{18}$ quaternary ammonium salt, preferably cetylpyridinium chloride.

The compositions of the present invention can be transparent or opaque, possess higher bio-availability and enhanced anti-dandruff efficacy at lower concentration of active(s), are stable at varying pH and humidity conditions and can be easily formulated into various personal care and industrial formulations.

An embodiment of the present invention is directed to a transparent or opaque stable biocidal composition comprising: (i) 0.5-35% w/w of ZPTO, (ii) 0-20% w/w of a $C_8$-$C_{18}$ quaternary ammonium salt, preferably cetylpyridinium chloride (iii) 0.5-20% w/w organic amines and/or alkanol amine, (iv) 0.5-60% w/w water soluble glycol/polyol/glycol ether/lactam or mixtures thereof, (v) 0-10% w/w of a dispersant and/or a rheology modifier and/or a suspending agent, (vi) 0-60% w/w of water.

DETAILED DESCRIPTION OF THE INVENTION

The present invention provides a stable biocidal composition with enhanced antifungal activity and efficacy. The present invention also provides a biocidal composition having one or more $C_8$-$C_{18}$ quaternary ammonium salt in addition to zinc pyrithione. The biocidal compositions of the present invention possess high bio-availability of zinc pyrithione. The compositions of the present invention is opaque or transparent.

The inventors of the present invention have surprisingly found that quaternary ammonium salt, in particular $C_8$-$C_{18}$ quaternary ammonium salt such as cetylpyridinium chloride (CPC) possess significant anti-*malassezia* or anti-dandruff activity alone and shows enhanced anti-dandruff activity in combination with lower concentrations of ZPTO. The compositions and formulations of the present invention possess superior anti-dandruff efficacy at lower concentrations of active (s), ZPTO and $C_8$-$C_{18}$ quaternary ammonium salt. The compositions of the present invention are stable and also impart better sensorial benefits.

The invention described herein in detail using the terms defined below unless otherwise specified.

The term "biocidal composition" as used herein refers to a solution, suspension and/or a dispersion comprising zinc pyrithione either alone or in combination with a $C_8$-$C_{18}$ quaternary ammonium salt wherein the said composition is capable of inhibiting microbial growth.

The term "stock" as used herein refers to a concentrated solution, suspension and/or a dispersion comprising zinc pyrithione either alone or in combination with a quaternary ammonium salt as active.

The term "zinc pyrithione concentrate" refers to an aqueous suspension of zinc pyrithione in an amount from 25-50% w/w.

The term "personal care formulation" as used herein refers to various toiletries and cosmetic preparation used for general health and hygiene and grooming. Examples of personal care formulation includes but are not limited to shower gel, soap, conditioners, body lotion and shampoo, anti-dandruff shampoo, anti-dandruff hair gel, and the like.

The term "$C_8$-$C_{18}$ quaternary ammonium salt" as used herein refers to salts of quaternary ammonium cations with anions. The quaternary ammonium cations are positively charged polyatomic ions in which a central nitrogen atom is attached to same or different four straight chain or branched alkyl group (having from 8-18 carbon atoms) or a pyridine nitrogen attached to $C_8$-$C_{18}$ alkyl group. Examples of $C_8$-$C_{18}$ quaternary ammonium salt includes but are not limited to methyltrioctyl ammonium chloride, cetyltrimethyl ammonium chloride, decyltrimethyl ammonium chloride, didecyldimethyl ammonium chloride, trimethyltetradecyl ammonium bromide; dodecyl(lauryl) pyridinium chloride, tetradecyl(myristyl) pyridinium chloride, hexadecyl(cetyl) pyridinium chloride, methyl- or ethyl-cetylpyridinium chloride and octadecyl(stearyl) pyridinium chloride; alkylbenzyldimethyl ammonium halides or benzalkonium halides with chain lengths of $C_8$-$C_{18}$, predominantly $C_{12}$ to $C_{16}$, like cetalkonium chloride, benzethonium chloride, lauralkonium halide and stearalkonium chloride.

The term "surfactant" as used herein refers to substances which lower the surface tension of the medium in which it is dissolved, and/or the interfacial tension with other phases, and, accordingly, is positively adsorbed at the liquid/vapour and/or at other interfaces. Surfactants have a hydrophobic (water repellent) part and a hydrophilic ('water loving') part. The hydrophobic part consists of an uncharged carbohydrate group that can be straight, branched, cyclic or aromatic. Depending on the nature of the hydrophilic part the surfactants are classified as anionic, cationic, non-ionic, or amphoteric.

The term "anionic surfactant" as used herein refers to those surfactants where the hydrophilic part consists of a negatively charged group like a sulphonate, sulphate or carboxylate the surfactant. Examples of anionic surfactant include but are not limited to sodium, potassium or ammonium salts of long chain sulphates having carbon chain lengths 6-14, preferably sodium lauryl sulfate (SLS), sodium laureth sulfate (SLES), triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, ammonium lauryl sulfate, ammonium laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, amino acid derived surfactants and combinations thereof.

The term "cationic surfactant" as used herein refers to those surfactants where the hydrophilic part consists of a positively charged group. Examples of cationic surfactant include but are not limited to cetyl pyridinium chloride, stearyl pyridinium chloride, methyl or ethyl cetyl pyridinium chloride, aralkyl ammonium halides such as benzyl triethyl ammonium chloride, benzalkonium chloride, cetalkonium chloride, benzethonium chloride, lauryltrimethyl ammonium halide, cetrimonium halide or cetyltrimethyl ammonium halide, glycidyltrimethylammonium halide, tallowtrimethyl ammonium chloride, cocotrimethyl ammonium chloride, vitamin B6 hydrochloride, behenyltrimethyl ammonium chloride (BTAC), octyltrimethyl ammonium chloride, octyldimethylbenzyl ammonium chloride, decyldimethylbenzyl ammonium chloride, stearyldimethylbenzyl ammonium chloride, didodecyldimethyl ammonium chloride, dioctadecyldimethyl ammonium chloride, dipalmitoylethyldimethyl ammonium chloride and combinations thereof.

The term "non-ionic surfactant" as used herein refers those surfactants where the hydrophilic part is not charged. Examples of non-ionic surfactant include, but are not limited to Lamesoft PO65, polyoxyethylene (20) sorbitan monooleate (Tween 80), polyoxyethylene (20) sorbitan monolaurate (Tween 20), ethoxylated sorbitan monolaurate (Crillet 180) and combinations thereof.

The term "amphoteric surfactant" as used herein refers to those surfactants wherein hydrophilic part can be either positively or negatively charges depending on the pH of the solution. They can act as anionic surfactant in an alkaline solution or as cationic surfactant in an acidic solution. Examples of amphoteric surfactant include but are not limited to cocamidopropyl betaine (CAPB) or cocamide DEA and combinations thereof.

The term "surfactant system" as used herein refers to one or more surfactants selected form anionic surfactant, cationic surfactant, non-ionic surfactant, amphoteric surfactants or a combination thereof.

The term "suspending agents", are as used herein refers to insoluble particles dispersed in a vehicle and help to reduce the sedimentation rate of particles in suspension. The term "dispersants" as used herein are substances which facilitate the dispersion of aggregates and improve the kinetic stability of the particles. The term "rheology modifiers" as used herein refers to compounds/polymers which alter the thickness or viscosity of the system. Throughout the specification, these terms have been used interchangeably. Examples of dispersants and/or rheology modifier and/or suspending agent as used herein include but are not limited to sodium and potassium salts of alkyl-aryl sulfonic acids and/or polymerized alkyl-aryl sulfonic acids and/or formaldehyde complexes, synthetic silicates, castor oil based thixotropes and organic thixoptropes, carboxymethylcellulose, organoclays, synthetic clays, polymers of acrylic acid cross-linked with polyalkenyl ethers or divinyl glycol, Stepan TAB-2, Stepan SAB-2, Carbopol ETD 2020, Carbopol Aqua SF-1, Carbopol Ultrez 20, Rheocare TTA, Rheocare C Plus, xanthum gum, dehydroxanthan gum like Amaze XT, methyl hydroxyethylcellulose like Structure Cell 12000 and combinations thereof. Sodium and potassium salts of alkyl-aryl sulfonic acids and/or polymerized alkyl-aryl sulfonic acids and/or formaldehyde complexes is selected from but not limited to Tytan series, Tysperse series, DARVAN Series, DEMOL Series, DAXAD Series, TAMOL Series, HAROL Series, LOMAR Series and the likes; synthetic silicates is selected from but not limited to sodium aluminium silicate, magnesium aluminum silicates and the likes; organoclays such as Claytone, Tixogel and the likes; synthetic clay such as Veegum, Laponite and the likes.

The term "suitable solvent" as used herein refers to cosmetically acceptable water and water miscible solvents such as glycol, polyol, glycol ethers, lactams and the like. Exemplary water miscible glycols/polyol/glycol ethers include but are not limited to propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme) and combinations thereof; exemplary lactams include but are not limited to 2-pyrrolidone, N-methyl pyrrolidone (NMP), polyvinylpyrrolidone (PVP) and combinations thereof.

In one embodiment, the present invention provides a transparent, stable biocidal composition of zinc pyrithione. The said composition comprises (i) 0.5-35% w/w of ZPTO, (ii) 0.5-20% w/w organic amines and/or alkanol amine, (iii) 0.5-60% w/w water soluble glycol/polyol/glycol ether/lactam or mixtures thereof, (iv) 0-10% w/w of a dispersant and/or a rheology modifier and/or a suspending agent, (v) 0-60% w/w of water.

In another embodiment, the present invention provides a transparent, stable biocidal composition of zinc pyrithione and a $C_8$-$C_{18}$ quaternary ammonium salt. The said composition comprises (i) 0.5-35% w/w of ZPTO, (ii) 0.05-20% w/w of a $C_8$-$C_{18}$ quaternary ammonium salt, (iii) 0.5-20% w/w organic amines and/or alkanol amine, (iv) 0.5-60% w/w water soluble glycol/polyol/glycol ether/lactams or mixtures thereof, (v) 0-10% w/w of a dispersant and/or a rheology modifier and/or a suspending agent, (vi) 0-60% w/w of water.

In yet another embodiment the present invention provides an opaque, stable biocidal composition of zinc pyrithione and a $C_8$-$C_{18}$ quaternary ammonium salt, preferably cetylpyridinium chloride. The said composition comprises (i) 0.01-10% w/w zinc pyrithione, (ii) 0.01-10% w/w $C_8$-$C_{18}$ quaternary ammonium salt, preferably cetylpyridinium chloride, (iv) 0.5-60% w/w water soluble glycol/polyol/ glycol ether/lactam or mixtures thereof, (v) 0-10% w/w of a dispersant and/or a rheology modifier and/or a suspending agent, (vi) 0-60% w/w of water.

The stable biocidal composition of the present invention and the formulations prepared from it, is in the form of a solution, suspension or dispersion. They are present in transparent or opaque form.

In a preferred embodiment the stable biocidal composition and the formulations prepared from the same are in transparent form. The transparent or opaque stable biocidal composition of the present invention as described herein can be incorporated into various personal care or industrial formulation.

In a preferred embodiment, the compositions of the present invention are incorporated into a personal care formulation.

In one embodiment the present invention provides personal care formulation comprising the 0.01% to 20% w/w of the transparent or opaque, stable biocidal composition of the present invention as described herein.

In another embodiment the present invention provides personal care formulation comprising 0.01% to 10% w/w of the transparent or opaque, stable biocidal composition of the present invention as described herein.

In a preferred embodiment the present invention provides a personal care formulation, said formulation comprising (i) 0.01-10% w/w transparent or opaque stable biocidal composition as described hereinabove, (ii) 5-45% w/w surfactant system, (iii) 15-75% water.

In yet another embodiment, the personal care formulation of the present invention further comprises one or more additional component selected from diluents, suspending agents, humectants, pH regulators, preservatives, perfumes, skin active agents and/or scalp modifiers, hair growth and/or hair loss preventive agents, sunscreens, UV absorbers, vitamins and/or herbal/fruit extracts.

In a preferred embodiment, the compositions of the present invention are incorporated into a hair care formulation.

In the most preferred embodiment, the compositions of the present invention are incorporated into an anti-dandruff hair care formulation.

In a yet another embodiment, the present invention provides a process for the preparation of stable biocidal compositions and their formulations, in particular personal care formulation.

In another embodiment, the present invention provides a process for preparing a transparent, stable biocidal composition as described hereinabove, said process comprising:
(a) adding an organic amine and/or alkanol amine to zinc pyrithione to obtain a mixture,
(b) adding a water soluble glycol/polyol/glycol ether/lactam or mixtures thereof to the mixture of step (a),
(c) preparing a solution of the $C_8$-$C_{18}$ quaternary ammonium salt, when present, in a suitable solvent and mixing it with a solution or suspension of dispersant,
(d) adding the mixture of step (b) to the homogenous solution of step (c).

In another embodiment, the present invention provides a process for preparing an opaque, stable biocidal composition as described hereinabove, said process comprising:
(a) preparing a solution of $C_8$-$C_{18}$ quaternary ammonium salt, preferably cetylpyridinium chloride in a suitable solvent and mixing it with a solution or suspension of dispersant to obtain a mixture,
(b) adding zinc pyrithione concentrate to mixture obtained in step (a), In yet another embodiment, the present invention provides a process for preparing a personal care formulation, said process comprising:
(a) preparing an aqueous solution of one or more surfactants,
(b) adding a dispersant and/or a rheology modifier and/or a suspending agent to the above solution,
(c) adding the opaque or transparent, stable biocidal composition as described hereinabove to the solution obtained in step (b)
(d) adding one or more additional component.

The suitable solvent used in the process of the present invention is selected from cosmetically acceptable water, propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme), 2-pyrrolidone, N-methyl pyrrolidone (NMP), polyvinylpyrrolidone (PVP) and combinations thereof.

In a preferred embodiment, the present invention provides a stable biocidal composition and/or personal care formulation wherein zinc pyrithione is present in an amount of 0.5% to 20% w/w.

In a preferred embodiment, the $C_8$-$C_{18}$ quaternary ammonium salt is selected from methyltrioctyl ammonium chloride, cetyltrimethyl ammonium bromide, cetylpyridinium chloride, dodecyl(lauryl) pyridinium chloride, tetradecyl (myristyl) pyridinium chloride, hexadecyl(cetyl) pyridinium chloride, methyl- or ethyl-cetylpyridinium chloride and octadecyl(stearyl) pyridinium chloride.

In the most preferred embodiment the $C_8$-$C_{18}$ quaternary ammonium salt is cetylpyridinium chloride. The cetylpyridinium chloride is anhydrous or monohydrate.

In a preferred embodiment of the present invention, the $C_8$-$C_{18}$ quaternary ammonium salt is present in an amount of 0.01% to 20% w/w.

The organic amines or alkanol amine used in the present invention is selected from the group comprising monoethanol amine (MEA), 3-aminopropyldimethyl amine, 3-methoxypropyl amine, bis-(2-hydroxypropyl) amine and combinations thereof; lactam is selected from 2-pyrrolidone, N-methyl pyrrolidone (NMP), polyvinylpyrrolidone (PVP) and combinations thereof.

In a preferred embodiment, the organic amines or alkanol amine is selected from one or more of monoethanol amine (MEA), N-methyl pyrrolidone (NMP), polyvinylpyrrolidone (PVP).

The water soluble glycols/polyol/glycol ethers used in the present invention is selected from propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme) and combinations thereof.

The compositions of the present invention can be transparent or opaque, possess higher bio-availability and anti-dandruff efficacy and at lower concentration of active(s), are stable at varying pH and humidity conditions and can be easily formulated into various personal care and industrial formulations.

The composition of the present invention can be incorporated into various personal care or industrial formulations such as for cutting oils and coolant systems, as an agent for protecting cellulosic fibers from loss of tensile strength due to action of fungi and as a preservative for water based paints, coatings, adhesives, wet-state preservatives, hard surface cleaners, hair care compositions, fabric care compositions, wood products, plastic products, medical products, fibers or any other antimicrobial application.

EXAMPLES

The invention is explained in detail in the following examples which are given solely for the purpose of illustration only and therefore should not be construed to limit the scope of the invention.

Example 1

Preparation of Transparent ZPTO Stock

To the weighed amount of ZPTO (w/w), monoethanolamine was added. Thereafter, NMP was added and contents were stirred with heating at 40-45° C. Propylene glycol, sorbitol and polyethylene glycol 400 were then added to the above mixture with continuous stirring to obtain the desired transparent composition. An exemplary composition obtained from the above process is tabulated below:

TABLE 1

Composition of transparent ZPTO stock

| Ingredients | 15% ZPTO Stock Solution | 10% ZPTO Stock Solution |
|---|---|---|
| ZPTO | 15% | 10% |
| Monoethanol amine | 10% | 7% |
| N-methyl pyrrolidone | 25% | 24% |
| Propylene glycol | 12% | 18% |
| Sorbitol | 9.5% | 8.5% |
| PEG 400 | 10% | 12% |
| Water | 18.5% | 20.5% |

Example 2

Preparation of Transparent ZPTO-CPC Stock

ZPTO solution was prepared by dissolving ZPTO, in monoethanol amine and NMP with stirring at 40-45° C. Similarly, CPC solution was prepared by dissolving in propylene glycol. This solution was added to an aqueous solution of dispersant (Tytan N) and sorbitol. To this solution, ZPTO solution was added slowly with continuous stirring to obtain the desired transparent composition. An exemplary composition obtained from the above process is tabulated below:

TABLE 2

Composition of transparent ZPTO - CPC stock:

| Ingredients | Quantity |
|---|---|
| ZPTO | 10% |
| Monoethanol amine | 10% |
| N-methyl pyrrolidine | 25% |
| CPC | 10% |
| Propylene glycol | 25% |
| Sorbitol | 3.5% |

TABLE 2-continued

Composition of transparent ZPTO - CPC stock:

| Ingredients | Quantity |
|---|---|
| Rheocare TTA | 1% |
| Tytan N | 0.5% |
| Water | 15% |

Example 3

Preparation of Opaque ZPTO-CPC Stock

CPC was dissolved in water in 1:2.5 ratio. A dispersant solution was also prepared. In a separate vessel, Ultrez 20 was sprinkled over the rest of water. After complete wetting (~5 min), contents were stirred at slow speed and then dispersant and CPC compound (10%) solutions were mixed. Mixture was stirred for 15 min at 40° C. Required amount of zinc pyrithione concentrate was added with continuous mixing at high rpm (600). This mixture was stirred for 30 min and finally a stable white suspension was obtained. An exemplary composition obtained from the above process is tabulated below:

TABLE 3

Composition of opaque stocks suspension of ZPTO and CPC:

| Ingredients | Quantity |
|---|---|
| ZPTO (48% suspension) | 10% |
| CPC | 10% |
| Ultrez 20 | 1.2% |
| Water | 75% |
| Tytan N | 3.8% |

Example 4

Preparation of Personal Care Formulation

In a 250 ml capacity kettle (thick walled beaker), weighed amount of SLES (2EO), SLS (Galaxy 780) and water were taken and heated till 55° C. with mixing to make a transparent homogenous mixture. To this hot mixture, weighed amount of suitable rheology modifier (Carbopol Aqua SF-1, Ultrez 20, Rheocare TTA etc.) was added slowly with continuous mixing. To this mixture, required amount of ZPTO solution from the stock solution (as prepared in example 1 or 2), was added drop-wise to obtain a transparent composition. The pH of the system was maintained in the range of 6.5-8. Thereafter, CAPB was added at 50° C., followed by addition of glycerin, hydrovance and aqueous solution of Merquat 3330 (conditioner) below 40° C. with continuous stirring. After addition of all above mentioned ingredients, fragrances compatible with aqueous system like Filip ES or Surf ES (Robertet) is added to the system at room temperature (25-30° C.). Total weight of kettle was taken and according to water loss, required amount of water was added. The mixture was stirred further for 10-15 min and was stored at room temperature in a container.

TABLE 4

Transparent hair care formulations

| Ingredients Used (in %) | Formulation | | | | | | | |
|---|---|---|---|---|---|---|---|---|
| | 1 | 2 | 3 | 4 | 5 | 6 | 7 | 8 |
| SLES (2EO-28%) | 20.00 | 22.50 | 27.00 | 24.50 | 30.00 | 30.50 | 30.00 | 28.50 |
| SLS (28%) | 8.00 | 10.00 | 9.70 | 10.75 | 8.75 | 10.00 | 11.00 | 10.00 |
| DI Water | 53.00 | 21.50 | 24.00 | 20.25 | 22.00 | 18.00 | 32.00 | 40.50 |
| Ultrez 20 | — | — | — | — | — | — | 3.25 | 4.50 |
| Carbopol Aqua SF-1 | 6.00 | 9.00 | 7.00 | — | — | — | — | — |
| Rheocare TTA | — | — | — | 5.25 | 6.50 | 8.00 | — | — |
| zinc Pyrithione | — | 2.00 (s) | 2.00 (s) | 2.00 (s) | 2.00 (15%) | 2.00 (10%) | — | — |
| ZPTO-CPC Mix | — | — | — | — | — | — | 2.00 (1:1) | 2.00 (1:1) |
| Monoethanol Amine | — | 12.75 | 1.00 | 2.50 | — | 0.50 | — | — |
| N-methyl Pyrrolidone | — | — | 8.50 | — | 4.50 | 4.00 | — | — |
| DEGMEE* | — | — | — | 20.50 | — | — | 2.25 | — |
| NaOH (18%) | 0.90 | — | — | — | — | — | — | 0.45 |
| CAPB | 6.00 | 5.00 | 6.00 | 5.00 | 8.00 | 8.00 | 6.00 | 8.00 |
| PEG 400 | 4.00 | 8.00 | 5.00 | 5.00 | 6.00 | 6.00 | 4.50 | — |
| Glycerin | — | — | — | 2.00 | — | 2.50 | 1 | — |
| PG** | — | — | 5.00 | — | 2.0 | 2.25 | 2.50 | 2.50 |
| Sorbitol | — | 2.00 | 2.00 | — | 4.00 | — | — | — |
| Hydrovance | 1.00 | 1.5 | 1.50 | — | 1.00 | 2.00 | 2.00 | 1.55 |
| Merquat Plus 3330 | 1.10 | 0.50 | 1.00 | 0.50 | 2.00 | 1.50 | 1.00 | — |
| Colaquat CCG | — | — | — | — | — | — | — | 2.00 |
| Neutralizer | — | 5.25 | 0.30 | 1.75 | 3.25 | 4.75 | 2.50 | — |
| Total formula | 100.00 | 100.00 | 100.00 | 100.00 | 100.00 | 100.00 | 100.00 | 100.00 |

*DEGMEE = Diethylene glycol monoethyl ether;
**PG = Propylene Glycol

Example 5

Physical Stability Studies of the Compositions Obtained in Examples 1-4

The stability of the compositions and their formulations with time and varying humidity conditions was tested and the results show that the compositions are stable in wide pH range (6.5-12) and show transparency of more than 90%.

Example 6

Antifungal/Anti-Dandruff Activity Studies

The anti-dandruff efficacy was determined by measuring zone of inhibition using disc diffusion method against *Malassezia furfur* (ATCC No. 14521). In this procedure, 10 µl of sample was added on the filter paper disc and the disc was kept in the microbial culture swabbed on the culture media. The culture plates were incubated at 37° C. for 48 hrs and antifungal activity was evaluated by observing an area of no growth around the disc. An area of no growth around the swatch is known as a zone of inhibition. The results are depicted in Table 5. Similarly, the anti-dandruff activities for ZPTO and ZPTO-CPC stock compositions and shampoo formulations against *M. furfur* have been done and data are summarized below in table 6:

TABLE 5

Anti-dandruff activities for various ZPTO containing samples against *M. Furfur*

| Example | Sample details | Quantity tested (in %) | Anti-dandruff (*M. furfur*) activity Zone of Inhibition (in mm) |
|---|---|---|---|
| 1 | ZPTO suspension in water | 2% | 20 mm |
| | ZPTO suspension in water | 0.2% | 20 mm |
| | ZPTO solution in MEA + NMP | 2% | 25 mm |
| | ZPTO solution | 0.2% | 25 mm |
| | ZPTO in surfactant + water | 2% | 20 mm |
| | ZPTO in surfactant + water | 0.2% | 20 mm |
| | ZPTO solution in surfactant + MEA + NMP | 2% | 25 mm |
| | ZPTO solution in surfactant + MEA + NMP | 0.2% | 25 mm |
| | Surfactant + water | 2% | No activity |
| | Surfactant + MEA + NMP + water | | No activity |

TABLE 6

Anti-dandruff activities for stock compositions and shampoo formulations against *M. furfur*

| Example | Sample Details | Quantity tested (%) | Anti-dandruff (M. furfur) activity Zone of Inhibition (in mm) |
|---|---|---|---|
| 1 | TSP ZPTO Stock (10%) | 2% | 45 |
|  | TSP ZPTO Stock (10%) | 1% | 42 |
|  | TSP ZPTO Stock (10%) | 0.5% | 42 |
|  | TSP ZPTO Shampoo (10%) | 0.5% | 40 |
|  | TSP ZPTO Shampoo (10%) | 2% | 48 |
|  | TSP ZPTO Shampoo (10%) | 1% | 45 |
|  | TSP ZPTO Stock (15%) | 2% | 48 |
|  | TSP ZPTO Shampoo (15%) | 2% | 45 |
| 2 | TSP ZPTO-CPC Stock (10-10%) | 1-1% | 64 |
|  | TSP ZPTO-CPC Stock (10-10%) | 0.5-0.5% | 54 |
|  | TSP ZPTO-CPC Shampoo (10-10%) | 1-1% | 65 |
|  | TSP ZPTO-CPC Shampoo (10-10%) | 0.5-0.5% | 52 |
| 3 | Opaque ZPTO Stock (48%) | 2% | 30 |
|  | Opaque ZPTO Stock (48%) | 1% | 28 |
|  | Opaque ZPTO Stock (48%) | 0.5% | 20 |
|  | Opaque ZPTO Shampoo (2%) | 2% | 25 |
|  | Opaque ZPTO Shampoo (2%) | 1% | 22 |
|  | Opaque ZPTO-CPC Stock (10-10%) | 1-1% | 55 |
|  | Opaque ZPTO-CPC Stock (10-10%) | 0.5-0.5% | 48 |
|  | Opaque ZPTO-CPC Shampoo (10-10%) | 1-1% | 52 |
|  | Opaque ZPTO-CPC Shampoo (10-10%) | 0.5-0.5% | 46 |
|  | TSP Shampoo (Blank) | — | No Activity |
|  | Opaque Shampoo (Blank) | — | No Activity |

*TSP: Transparent

We claim:

1. A transparent, stable biocidal composition, said composition comprising:
   (i) 0.5-35% w/w of zinc pyrithione,
   (ii) 0-20% w/w of $C_8$-$C_{18}$ quaternary ammonium salt,
   (iii) 0.5-20% w/w organic amines and/or alkanol amine,
   (iv) 0.5-60% w/w water soluble glycol/polyol/glycol ether/lactam or mixtures thereof,
   (v) 0-10% w/w of a dispersant and/or a rheology modifier and/or a suspending agent, and
   (vi) 0-60% w/w of water.

2. A transparent, stable biocidal composition, said composition comprising:
   (i) 0.5-35% w/w of zinc pyrithione,
   (ii) 0.05-20% w/w of a $C_8$-$C_{18}$ quaternary ammonium salt, preferably cetylpyridinium chloride,
   (iii) 0.5-20% w/w organic amines and/or alkanol amine,
   (iv) 0.5-60% w/w water soluble glycol/polyol/glycol ether/lactam or mixtures thereof,
   (v) 0-10% w/w of a dispersant and/or a rheology modifier and/or a suspending agent, and
   (vi) 0-60% w/w of water.

3. An opaque, stable biocidal composition, said composition comprising:
   (i) 0.01-20% w/w zinc pyrithione,
   (ii) 0.01-20% w/w $C_8$-$C_{18}$ quaternary ammonium salt, preferably cetylpyridinium chloride,
   (iii) 0.5-60% w/w water soluble glycol/polyol/glycol ether/lactam or mixtures thereof,
   (iv) 0-10% w/w of a dispersant and/or a rheology modifier and/or a suspending agent, and
   (v) 0-60% w/w of water.

4. A personal care formulation comprising the transparent or opaque stable biocidal composition as claimed in claim 1, 2 or 3.

5. A personal care formulation, said formulation comprising:
   (i) 0.01-10% w/w transparent or opaque, stable biocidal composition as claimed in any one of claim 1, 2 or 3,
   (ii) 5-45% w/w surfactant system, and
   (iii) 15-75% water.

6. The stable biocidal composition as claimed in any of the claims 1 to 3, wherein the $C_8$-$C_{18}$ quaternary ammonium salt is cetylpyridinium chloride.

7. The stable biocidal composition as claimed in any one of claims 1 to 3, wherein the said composition is in the form of a solution, suspension or dispersion.

8. The stable biocidal composition as claimed in any one of claims 1 to 3, wherein zinc pyrithione is present in an amount of 0.5% to 20% w/w.

9. The stable biocidal composition as claimed in any one of claims 1 to 3, wherein the $C_8$-$C_{18}$ quaternary ammonium salt is present in an amount of 0.01% to 20% w/w.

10. The stable biocidal composition as claimed in any one of claims 1 to 3, wherein the $C_8$-$C_{18}$ quaternary ammonium salt is selected from the group consisting of methyltrioctyl ammonium chloride, cetyltrimethyl ammonium bromide, cetylpyridinium chloride, dodecyl(lauryl) pyridinium chloride, tetradecyl(myristyl) pyridinium chloride, hexadecyl (cetyl) pyridinium chloride, methyl- or ethyl-cetylpyridinium chloride and octadecyl(stearyl) pyridinium chloride.

11. The stable biocidal composition as claimed in any one of claims 1 to 3, wherein the organic amines or alkanol amine is selected from the group consisting of monoethanol amine (MEA), 3-aminopropyldimethyl amine, 3-methoxypropyl amine, bis-(2-hydroxypropyl) amine and combinations thereof.

12. The stable biocidal composition as claimed in any one of claims 1 to 3, wherein the water soluble glycols/polyol/glycol ethers are selected from the group consisting of propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme) and combinations thereof; lactam is selected from 2-pyrrolidone, N-methyl pyrrolidone (NMP), polyvinylpyrrolidone (PVP) and combinations thereof.

13. A personal care formulation as claimed in claim 4, further comprising one or more additional components including diluents, suspending agents, humectants, pH regulators, preservatives, perfumes, skin active agents and/or scalp modifiers, hair growth and/or hair loss preventive agents, sunscreens, UV absorbers, vitamins, herbal extracts and the like.

14. A process for preparing a transparent stable biocidal composition as claimed in claim 1 or 2, said process comprising:
   (a) adding an organic amine and/or alkanol amine to zinc pyrithione to obtain a mixture, (b) adding a water soluble glycol/polyol/glycol ether/lactam or mixtures thereof to the mixture of step (a),
(c) preparing a solution of the $C_8$-$C_{18}$ quaternary ammonium salt, when present, in a suitable solvent and mixing it with a solution or suspension of dispersant, and
(d) adding the mixture of step (b) to the homogenous solution of step (c).

15. A process for preparing an opaque stable biocidal composition as claimed in claim 3, said process comprising:
   (a) preparing a solution of $C_8$-$C_{18}$ quaternary ammonium salt, preferably cetyl-pyridinium chloride in a suitable solvent and mixing it with a solution or suspension of dispersant to obtain a mixture, and
   (b) adding zinc pyrithione concentrate to mixture obtained in step (a).

16. A process for preparing a personal care formulation comprising:
   (a) preparing an aqueous solution of one or more surfactants,
   (b) adding dispersant and/or a rheology modifier and/or a suspending agent to the above solution,
   (c) adding the stable biocidal composition as claimed in any one of claims 1 to 3 to the solution obtained in step (b) and
   (d) adding one or more additional component.

17. The process as claimed in claim 14, wherein the suitable solvent is selected from the group consisting of cosmetically acceptable water, propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme), 2-pyrrolidone, N-methyl pyrrolidone (NMP), polyvinylpyrrolidone (PVP) and combinations thereof.

18. The biocidal composition as claimed in any one of claim 1, 2 or 3, as and when used in the preparation of hair care formulations, in particular anti-dandruff hair care formulations.

19. The biocidal composition as claimed in any one of claim 1, 2 or 3, as and when used as a biologically active agent for cutting oils and coolant systems, as an agent for protecting cellulosic fibers from loss of tensile strength due to action of fungi and as a preservative for water based paints, coatings, adhesives, wet-state preservatives, hard surface cleaners, fabric care compositions, wood products, plastic products, personal care formulations, medical products, fibers or any other antimicrobial application.

20. The personal care formulation of claim 4, wherein the formulation is in the form of a solution, suspension or dispersion.

21. The process as claimed in claim 15, wherein the suitable solvent is selected from the group consisting of cosmetically acceptable water, propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme), 2-pyrrolidone, N-methyl pyrrolidone (NMP), polyvinylpyrrolidone (PVP) and combinations thereof.

* * * * *